(12) United States Patent
George

(10) Patent No.: US 6,929,628 B2
(45) Date of Patent: Aug. 16, 2005

(54) FLUSHABLE ABSORBENT ARTICLE

(76) Inventor: Frederick W. George, 117 Memorial Avenue, Christchurch 8004 (NZ)

( * ) Notice: Subject to any disclaimer, the term of this patent is extended or adjusted under 35 U.S.C. 154(b) by 346 days.

(21) Appl. No.: 10/128,645

(22) Filed: Apr. 22, 2002

(65) Prior Publication Data

US 2003/0216704 A1 Nov. 20, 2003

(51) Int. Cl.⁷ ................................................ A61F 13/15
(52) U.S. Cl. .............................. 604/385.11; 604/385.13
(58) Field of Search ............ 604/385.11, 385.13–385.16

(56) References Cited

U.S. PATENT DOCUMENTS

| | | | | |
|---|---|---|---|---|
| 4,964,857 A | * | 10/1990 | Osborn ........................ | 604/395 |
| 5,026,363 A | * | 6/1991 | Pratt ...................... | 604/385.21 |
| 5,405,342 A | * | 4/1995 | Roessler et al. ............. | 604/364 |
| 5,830,201 A | * | 11/1998 | George et al. ............... | 604/364 |
| 6,444,761 B1 | * | 9/2002 | Wang et al. ................. | 525/404 |
| 6,623,466 B1 | * | 9/2003 | Richardson ............ | 604/385.19 |
| 6,659,993 B2 | * | 12/2003 | Minato et al. ......... | 604/385.27 |

* cited by examiner

*Primary Examiner*—Larry I. Schwartz
*Assistant Examiner*—C. Lynne Anderson
(74) *Attorney, Agent, or Firm*—Richard E. Backus

(57) ABSTRACT

A toilet flushable diaper for use by infants and incontinent adults. The diaper has a liquid impervious back sheet comprised of a soluble film center layer covered on both sides with flocking or nonwoven material. An absorbent member is carried on the inner surface of the back sheet comprises a liquid pervious cover which encapsulates an inner body for absorbing urine and other body fluids. The diaper is formed with a weakened tear sheet which enables manual tearing of it into several pieces, allowing the pieces to dissolve when absorbing water as they are flushed down a toilet.

2 Claims, 3 Drawing Sheets

FLUSHABLE ABSORBENT ARTICLE

FIELD OF THE INVENTION

The present invention relates to completely flushable absorbent articles such as flushable diapers, for use with infants or incontinent adults. More particularly, the invention relates to diaper construction, componentry, and method for flushing the soiled diaper down a modern water conserving six litre flush household toilet

BACKGROUND OF THE INVENTION

Absorbent articles such as flushable diapers exist to absorb and isolate human infectious waste. All human waste, even that of healthy individuals, is always dangerous infectious waste. To prevent contagious disease, public health and safety regulations require that this human sewerage be kept separate from the environment until rendered harmless in a proper closed treatment system. Most human diseases are species specific, meaning that they are not contagious across species, and can only be contracted from another human being. For this reason, normal environmental contamination from other animal waste, whether household pets, farm animals, or aquatic animals, although of concern, is not the serious risk to human life and health.

Completely flushable diapers are convenient and safe, not only for the general public, in contradistinction to disposable diapers, but for the individual caretaker as well, minimizing the handling normally required with traditional laundered cloth diapers. In order to conserve water, modern toilet technology has reduced cistern capacity and maximum single flush volume to six liters (by Federal statute in the United States). This restricted flush volume makes the task of easily and consistently flushing a soiled diaper down the toilet problematic.

OBJECTS AND SUMMARY OF THE INVENTION

It is a general object of the invention to provide a unitary, completely toilet flushable, wastewater dissolving absorbent article for use on the body of an infant or adult.

The invention employs several distinct inventive steps, which when uniquely combined create flushable diapers that are easily and consistently flushed down any toilet without causing blockage. The completely flushable diaper is made of materials which are known to be inert or capable of being rendered harmless, and which degrade in a metropolitan sewerage treatment system or individual homeowner septic system.

The invention provides a liquid impervious back sheet made up of a water soluble film central layer coated on both sides with an insoluble layer. This liquid impervious back sheet thence covered on both sides with an intermittent flocking or nonwoven material. Wastewater soluble elastic members secure a close fit. An absorbent member carried on the inner surface of the back sheet comprising a water pervious cover encapsulating an inner body comprised of a sufficiently hydrophilic material to absorb urine and other bodily fluids. Manually this absorbent member is ruptured, the enclosed hydrophilic material removed into the toilet, to dissolve in the wastewater. A significant portion of the insoluble coating is removed from the water soluble film central layer of the liquid impervious backsheet, allowing it to dissolve when deposited in the wastewater. The absorbent article is manually torn into separate pieces, flushed down the toilet sequentially, in multiple flushes, or partially torn, creating a single long narrow piece which is fed progressively into the wastewater as the toilet flushes. All parts of the used diaper are flushed down the toilet. No part is discarded in any other way.

DESCRIPTION OF THE PREFERRED EMBODIMENTS

As used herein, the term "unitary, completely toilet flushable, wastewater dissolving absorbent article" describes articles that absorb and isolate human exudates by fitting closely to the anatomical source of the exudate. Moreover, such articles are single use items, removed after soiling, and wholly flushed down a toilet, partially dissolving in the wastewater where they are ultimately degraded and rendered harmless. They are unitary in that they do not contain separate parts that are assembled prior to use or retained after flushing. As used herein, the term "diaper" describes generally such an item worn by infants or incontinent adults, including partially absorbent articles designed to assist in toilet training.

Figure 1:
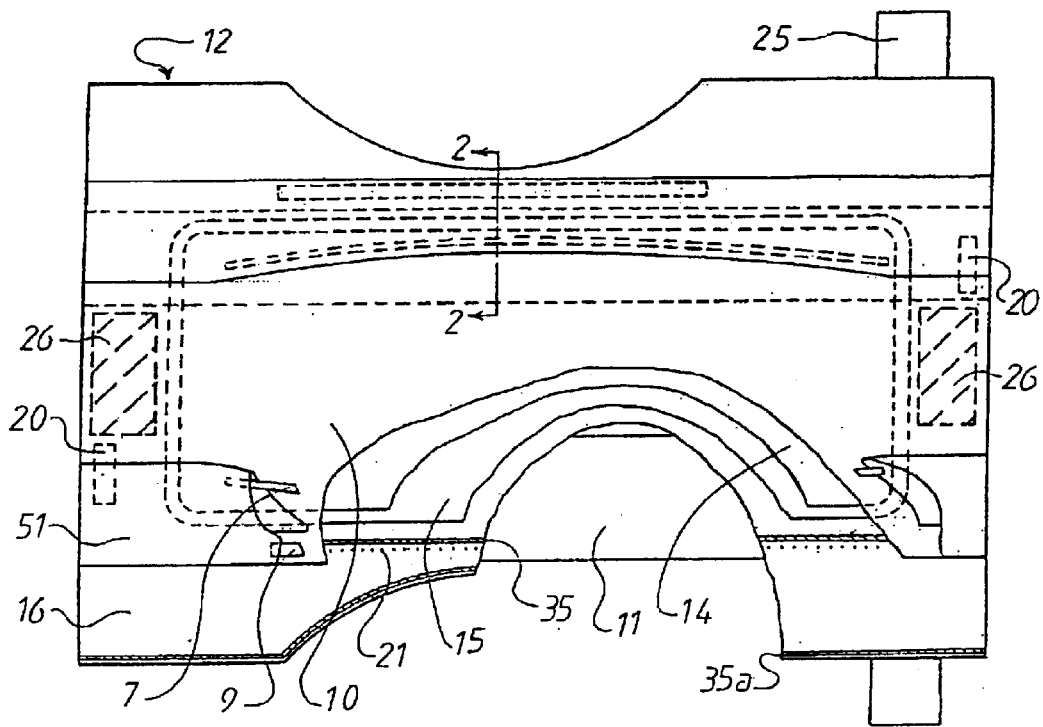
FIG. 1 is a Top View (the surface in contact with the wearer) of an essentially bilaterally symmetrical, unitary, completely toilet flushable, wastewater dissolving absorbent article showing underlying structures with dashed lines on one side, the other side showing underlying structures with successive layers torn away.

FIG. 1 is a Top View (the surface in contact with the wearer) of the diaper 12 stretched flat with slight contraction demonstrated in the elastics. Diaper 12 is bilaterally symmetrical, except for tear strip 11 reinforcing glue patch 20. One side of FIG. 1 outlines underlying structures with dashed lines; the other side shows successive layers torn away, revealing underlying structures.

Figure 2:
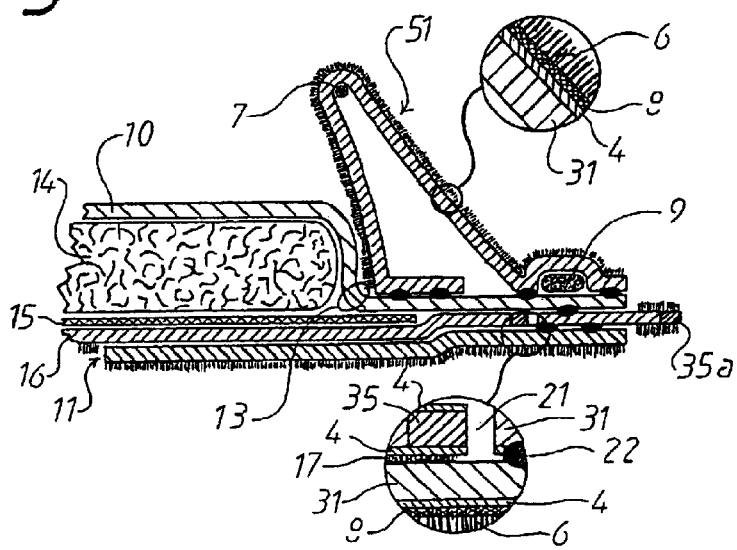
FIG. 2 is a Partial Cross Section View at section line 2—2 of FIG. 1.

Closed standing triangular prism cuff 51 is made of polyvinyl alcohol (PVOH) or similar water soluble film 31. of Partial Cross Section View FIG. 2, generally 20–30 microns in thickness, in the shape of a closed standing prism, with the two separate proximal edges forming the base of the triangular prism, glued to the underlying top sheet 10. This triangular prism shape of the standing cuff is positioned to closely fit the inguinal skin fold, snugly filling the triangular concave space where the medial portion of the thigh meets the perineal region. This triangular cross section standing cuff 51 of FIG. 2 provides a single, large contact area sealing fit, for enhanced prevention of leakage of bodily exudates from around the lateral edges of the diaper. This provides a superior sealing system to the existing prior art, namely paper thin single or double cuffs with linear contact area paper edges, which also cause uncomfortable and unsightly skin indentations on the infant from the excessive elastic pressure along the narrow raised edge. Contained within the closed standing triangular prism cuff 51 are linear elastic contractile members 7,9 for maintaining the upright shape of said cuff, keeping the distal edge away from the two separate proximal edges when curved and wrapped around the infant, controlling the fit of the diaper. These linear elastic contractile members are made of a water soluble elastic polymer, PVOH or similar, within the closed standing triangular prism cuff 51. While the diaper is worn these water soluble elastic members 7,9 are protected from moisture and body exudates because they are within the closed standing triangular prism cuff 51. When the diaper is flushed down the toilet, the linear elastic water soluble contractile members 7, 9 exposed by the peeling away of the tear strip 11, dissolve in the waste water.

Transverse elastic water soluble contractile members 26 similarly control the fit of the diaper at the waist. These elastic members may be placed external to the liquid impervious backsheet 16, protecting them from moisture and body exudates while the diaper is worn, or the may be placed between the liquid impervious backsheet 16, and the topsheet 10. When the diaper is flushed down the toilet, the transverse elastic water soluble contractile members 26 exposed by the peeling away of the tear strip 11, and dissolution and breakdown of the liquid impervious backsheet 16, dissolve in the waste water.

The PVOH film of the closed standing triangular prism cuff has a thin durable water insoluble continuous coating 4 of FIG. 2 of poly (vinylidene) dichloride (PVDC), which is a copolymer of polyvinyl chloride and vinylidene chloride, or similar durable water insoluble continuous coating, generally 5–15 microns in thickness, on the external surface. Bonded directly into this water insoluble coating 4, or utilizing an additional bonding layer of adhesive 8, is an interspersed flocking covering 6. These flocking fibres may be of synthetic materials such as nylon or polyester, or natural fibres such as cellulose or cotton. They may be adhered as individual fibres or clustered in groups, fixed at right angles to the plane of the PVOH film 31 or at various angles including lying flat on the film. This surface adhered flocking covering 6 is usually applied during the process of applying the insoluble coating 4, although it may be applied afterwards using an additional layer of adhesive 8. Application may be by standard electrostatic or mechanical means commonly used in the flocking industry. This provides a soft, comfortable velour-cloth-like textural surface against the wearer's skin in the inguinal skin fold, thigh, and perineum.

Removal of tear strip 11, exposes the inner uncoated surface of the PVOH film 31 closed standing triangular prism cuff 51 to waste water in the toilet. This uncoated PVOH film 31 rapidly dissolves, removing the sole supportive structural integrity of the durable insoluble coating 4, additional layer of adhesive 8 (if present), and interspersed flocking covering 6. With the dissolution of the PVOH film 31 the durable water insoluble continuous coating 4 and additional layer of adhesive 8 (if present), fracture into small (less than 5 mm across) flakes of material. The interspersed flocking covering 6 breaks into clumps of, and individual fibres.

Figure 5:
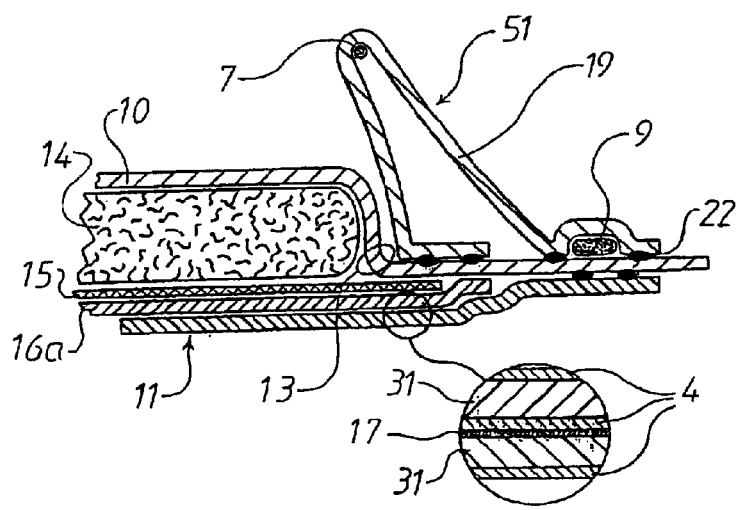
FIG. 5 is a Partial Cross Section View at section line 5—5 of FIG. 4.

In the second embodiment of the invention, Partial Cross Section View FIG. 5, the closed standing triangular prism cuff is made instead of a hydrophobic nonwoven synthetic or natural fibre material 19, well known in the art. This material restricts moisture and body exudate penetration, preventing leakage either into the closed standing triangular prism cuff, or across it to the lateral edge of the diaper.

Figure 3:
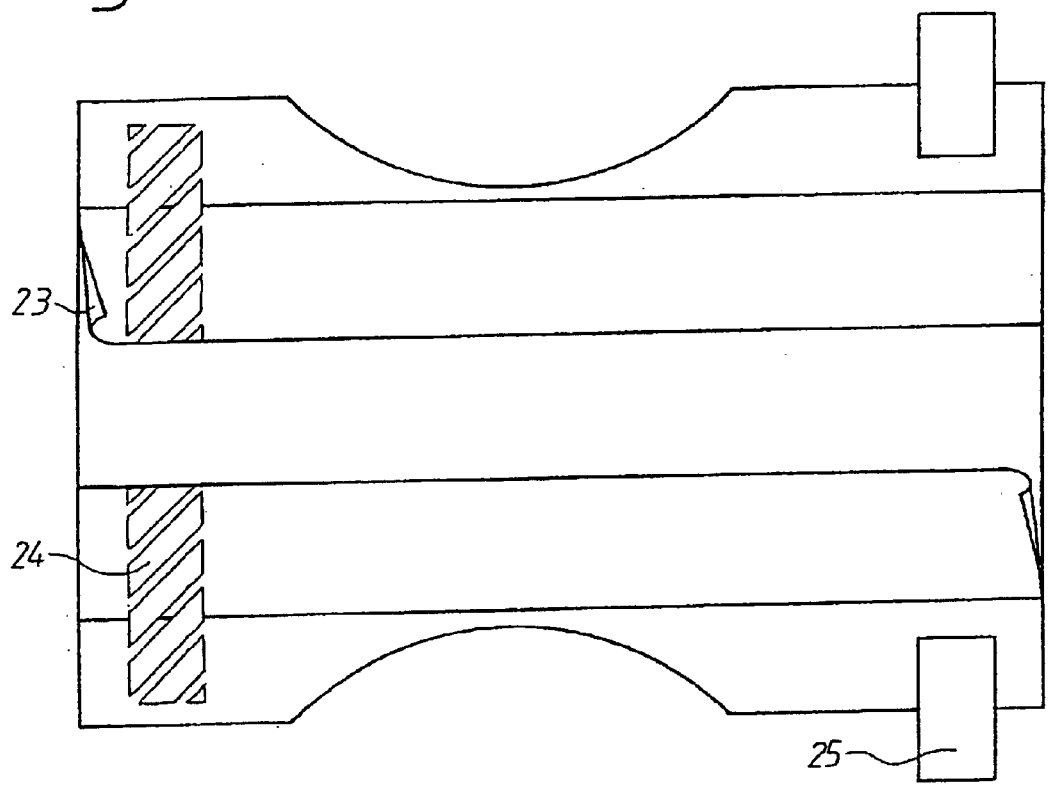
FIG. 3 is a Bottom View (the exterior surface) of FIG. 1 and FIG. 4.
Figure 4:
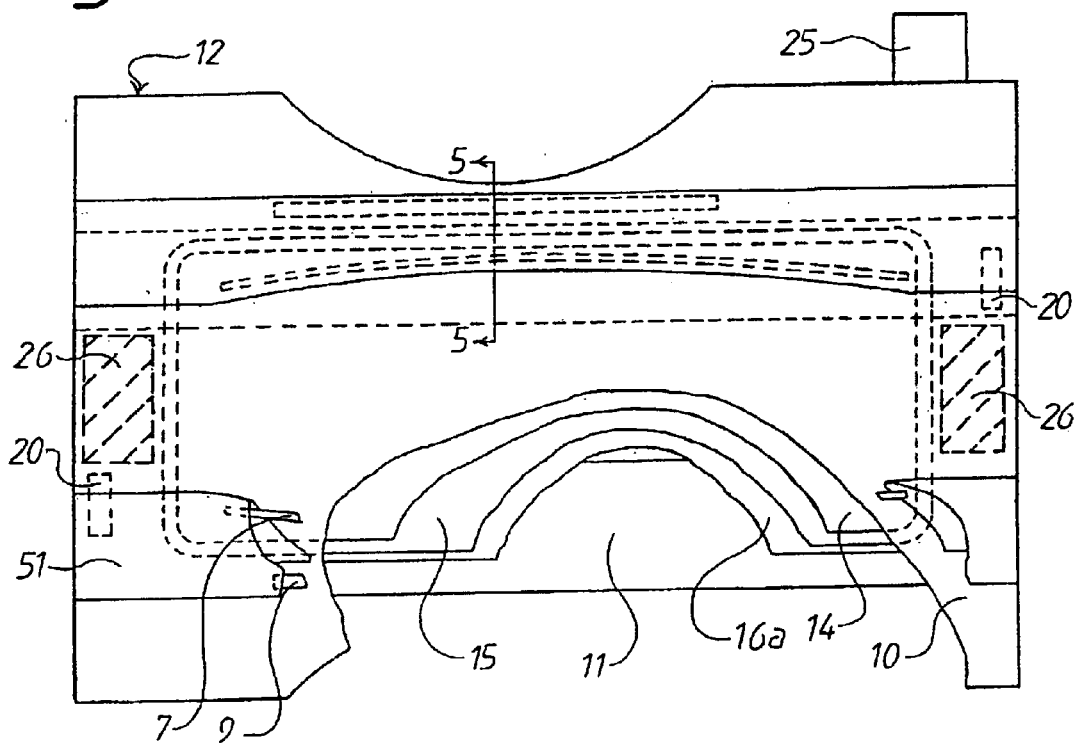
FIG. 4 is a Top View of a second embodiment of the absorbent article in FIG. 1.

In either the first embodiment, FIG. 3 or the second embodiment, FIG. 4; there are contained within the closed standing triangular prism cuff 51 linear elastic contractile members 7, 9 for maintaining the upright shape of said cuff, keeping the distal edge away from the two separate proximal edges. These linear elastic contractile members are made of a water soluble elastic polymer, PVOH or similar, within the closed standing triangular prism cuff 51. While the diaper is worn these water soluble elastic members 7, 9 are protected from moisture and body exudates because they are within the closed standing triangular prism cuff 51. When the diaper is flushed down the toilet, the linear elastic contractile members 7, 9 exposed by the peeling away of the tear strip 11, dissolve in the wastewater.

The closed standing triangular prism cuff 51 is bonded to the underlying top sheet 10 using hot glue or other adhesive well known in the art. Each end may be sealed closed medially and flattened to the surface of the underlying top sheet 10 with hot glue or other adhesive to form a more cup-shaped compartment between the closed triangular standing prism cuffs, helping to contain moisture and body exudates.

The top sheet 10 is made of hydrophilic spunbonded nonwoven synthetic or natural fibres, such as polypropylene or cellulose, or a combination thereof, well known in the art. This material has significant wet strength, containing the loose absorbent body material 14 when it is wetted by body exudates.

Tearing the top sheet 10 along the edge of the length of the absorbent body 14 at location 13 releases the loose absorbent body material 14 into the toilet for flushing. Location 13 is determined as a weakened tear path by the directional tearing nature of the top sheet spunbonded nonwoven material and the diaper construction causing a stress riser next to the glued proximal medial edge of the standing triangular prism cuff 51.

Absorbent body 14 is made up of hydrophilic cellulose fluff pulp and super absorbent polymer, well known in the art. This combination absorbs moisture and body exudates sufficiently while maintaining structural integrity. When placed in the toilet wastewater, the wastewater is absorbed to such an extent that structural integrity is lost, the absorbent body 14 breaking down into small fibre pieces and colloid that is easily flushed.

Hydrophobic sheet 15, made of nonwoven synthetic or natural fibres, or as a flocking-like coating applied to the adjacent surface of the liquid impervious backsheet 16, insulates the liquid impervious backsheet from direct contact with the moisture and free droplets of liquid of the absorbent body 14. This allows a thinner application of insoluble coating 4 to be used in the diaper construction, maintaining the liquid impervious property of the liquid impervious backsheet 16, and yet enabling the thin insoluble coating 4 to more easily fracture into small pieces when the supporting structure of the PVOH film 31 is dissolved away.

The liquid impervious backsheet 16 is made up of PVOH film, generally 20–30 microns in thickness, coated on each surface (top surface and back surface) with the previously described durable water insoluble continuous coating 4, 5–15 microns in thickness. The top surface coating may be reinforced with heavier or additional durable water insoluble continuous coating, 5–10 microns in thickness, along and just inward of the side edges along the length of the absorbent body 14 when the absorbent body is at its maximum absorbent capacity. This is to prevent the premature breakdown and dissolution of the impervious backsheet in this area of increased tractional and frictional stress caused by the side edges of the absorbent body 14 along its length.

These linear stripes 30–60 millimeters in width of thicker insoluble coating reinforce the top surface of the liquid impervious backsheet 16 in the area of increased stress, and yet allow the insoluble coating 4 on the rest of the liquid impervious backsheet 16 to remain as thin as practicable for easy fracture into small pieces during dissolution in the wastewater.

Bonded directly into this durable water insoluble continuous coating 4, or utilizing an additional bonding layer of adhesive 8, is an interspersed flocking covering 6 applied to the interior surfaces of the liquid impervious backsheet 16 that come in contact with the wearer's skin, and the exterior surface of the diaper. These fibres may be of synthetic materials such as nylon or polyester, or natural fibres such as cellulose or cotton. They may be adhered as individual fibres or clustered in groups, fixed at right angles to the plane of the PVOH film 31 or at various angles including lying flat on the film. This surface adhered flocking covering 6 is usually applied during the process of applying the insoluble coating 4, although it may be applied afterwards using an additional layer of adhesive 8. Application may be by standard electrostatic or mechanical means commonly used in the flocking industry. This provides a soft, comfortable velour-cloth-like textural surface against the wearer's skin and on the exterior surface of the diaper.

In the second embodiment of the invention, FIG. 5, the liquid impervious backsheet 16a does not have the interspersed noncontinuous fabric-like covering 6. The interior surface of said backsheet does not come in direct contact with the wearer's skin.

Liquid impervious backsheet 16 has a lengthwise line of perforations 21 on both sides of the diaper beneath the closed standing triangular prism cuff 51. Peeling away the tear strip 11 simultaneously tears the nappy along the line of perforations 21 separating the nappy into multiple separate or contiguous parts because the lateral edge of tear strip 11 is securely bonded with hot glue 22 or similar adhesive to the underlying liquid impervious backsheet 16 just lateral to the line of perforations 21.

Liquid impervious backsheet 16 has annealed segment portions 35, 35a to control solubility of the PVOH film. During the manufacturing process heat is applied to a 1–4 millimeter wide linear segment of the PVOH film, raising its temperature to between 150–200 degrees Celsius, rendering said annealed portion relatively less soluble. This heat treatment is applied to the impervious backsheet 16 at annealed segment portion 35 to block moisture or bodily exudates which may enter through perforations 21 from penetrating and dissecting medially between the surface insoluble coating layers 4 by dissolving the PVOH film 31. Similarly, liquid impervious backsheet 16 is annealed at segment portion 35a to block moisture or bodily exudates from entering at the cut raw edge of backsheet 16, penetrating and dissecting medially between the surface insoluble coating layers 4 by dissolving the PVOH film 31.

In the first embodiment of the invention tear strip 11 is made up of PVOH film, generally 20–30 microns in thickness, coated with a pressure sensitive contact adhesive (that adheres on contact) 17 on the top surface, the portion medial to the overlying line of perforations 21 of FIG. 2. Tear strip 11 commonly is approximately 25–40 millimeters in width. The bottom surface is coated with the previously described insoluble coating 4, 5–15 microns in thickness. Bonded directly into this water insoluble coating 4, or utilizing an additional bonding layer of adhesive 8, is the previously described interspersed flocking covering 6. The lateral edge of tear strip 11 is securely bonded with hot glue 22 or similar adhesive to the underlying liquid impervious backsheet 16 just lateral to the line of perforations 21.

Tear strip 11 additionally reinforces liquid impervious backsheet 16, 16a, preventing its premature breakdown and dissolution in this area of increased tractional and frictional stress from the side edges of the absorbent body 14 along its length. This reinforcement is available when necessary while the diaper is in use, and then is conveniently peeled away so that the durable water insoluble continuous coating 4 on the liquid impervious backsheet can remain as thin as practicable for easy fracture into small pieces during dissolution in the wastewater.

The pressure sensitive contact adhesive 17 is of such a nature that it adheres to the uncoated PVOH film on the top surface of the tear strip 11 and the insoluble coating 4 of the liquid impervious backsheet 16, 16a with greater tenacity than the insoluble coating 4 adheres to the underlying PVOH film of the liquid impervious backsheet 16, 16a. When the tear strip 11 is peeled away from the liquid impervious backsheet 16, 16a, the insoluble coating 4 adheres to the contact adhesive 17 which adheres to the tear strip 11, pulling off the insoluble coating from the underlying PVOH film of the liquid impervious backsheet 16, 16a. This exposes a significant portion of the uncoated PVOH film of the backsheet, allowing rapid dissolution in the wastewater.

Using another assembly technique, instead of tear strip 11 being coated with pressure sensitive contact adhesive 17 on the top surface, as described above, the uncoated tear strip may be placed directly on the uncoated PVOH film surface, both the tear strip and the PVOH film having the durable water insoluble continuous coating 4 applied on their exterior surfaces during the manufacturing of the liquid impervious backsheet 16, 16a. Subsequently, when the tear strip is peeled away from the liquid impervious backsheet, a significant portion of the uncoated PVOH film of the backsheet is exposed beneath the tear strip, allowing rapid dissolution of the backsheet in the wastewater.

Using an additional assembly technique, tear strip 11 may be a nonwoven or similar material laminated directly to the durable water insoluble continuous coated liquid impervious backsheet 16, 16a with hotmelt adhesive.

In the second embodiment of the invention, FIG. 5, the top surface of tear strip 11 is coated with pressure sensitive contact adhesive 17 on the portion immediately beneath the overlying liquid impervious backsheet 16a. The lateral edge of tear strip 11 is securely bonded at 22 with hot glue or similar adhesive.

These, and other various techniques of a similar nature, designed to remove a significant portion of durable water insoluble continuous coating 4 from the water soluble film 31 providing sole supportive structural integrity to the durable water insoluble continuous coating 4, are understood to be in the spirit or essence of the invention.

Figure 6:
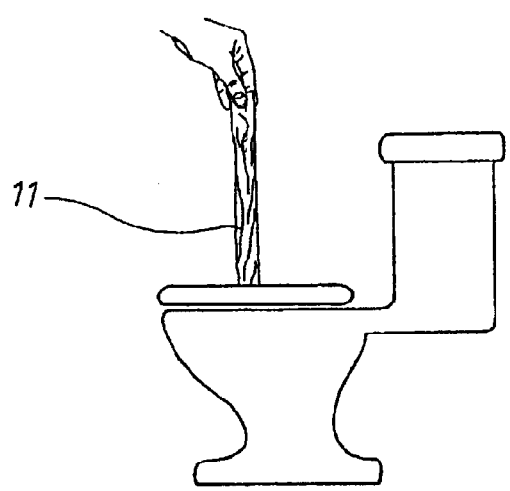
FIG. 6 is a Perspective View of the method of progressively feeding the absorbent article of FIG. 1 or FIG. 4.

In either embodiment, Bottom View FIG. 3 or Bottom View FIG. 6, tear strip 11 is peeled away at tab 23 and pulled away along the length of the exterior surface of the diaper down to reinforcing glue patch 20, which prevents tear strip 11 from easily being completely separated from the diaper. Reinforcing glue patch 20, may be a water soluble adhesive such that although it secures tear strip 11 from being easily completely separated when discarding the diaper in the toilet, subsequently glue patch 20 dissolves in the wastewater, allowing the multiple contiguous parts to separate for ease of transport in the wastewater drain pipe.

In the first embodiment of the invention, FIGS. 1, 2, along with tear strip 11 the portion of the nappy lateral to line of perforations 21 comes away at said line of perforations and the standing triangular prism cuff 51 comes away at weakened tear path 13.

In the second embodiment of the invention, FIGS. 4, 5, along with tear strip 11 both the standing triangular prism cuff 51 and the lateral portion of the diaper come away at weakened tear path 13.

Although it is possible to completely separate tear strip 11 and the associated lateral portion and standing triangular prism cuff 51 away from the diaper, under most circumstances the preferred method is leave this attached at glue patch 20. After each tear strip 11 is peeled away in opposite directions, the torn elongated diaper becomes approximately three times as long and approximately one third as wide as the original diaper.

When the tear strips 11 are peeled away removing a significant portion of insoluble coating 4, simultaneously the top sheet 10 is torn at location 13 opening the envelope containing the absorbent body 14. The loose absorbent body material is dropped into the toilet. Next, the diaper is held by the free end of the tear strip 11, over the toilet FIG. 6, while the free end of the opposite tear strip 11 is dipped into the wastewater in the toilet bowl. The toilet is flushed, and as the water empties, the elongated diaper is gradually fed into the toilet as the flowing water floats and tugs the diaper down the drain. Because the diaper is held in traction in the flushing water, it remains elongated as it floats and passes through the drain trap, being pulled along by the flushing water. This method for flushing a unitary, completely toilet flushable, wastewater dissolving absorbent article diaper down the toilet is a new, not obvious, and unique inventive step.

In fact, normally a flush toilet develops a charge of water behind the material to be flushed (which should be clumped or crumpled into a mass), pushing the material through the drain trap and down the drainpipe. Indeed, a published paper states "At these low solid velocities the continuing transport is entirely dependent on the retention of a water volume behind the solid." (Howarth et. al., Development of a Flushability Criterion for Sanitary Products, June 1980, page 9, Brunel University, Uxbridge, England) The effective clearing of the material from the toilet (w.c.) is dependent on how early in the flush cycle the material exits the toilet (an earlier exit leaves a greater trailing water volume). "Both these (deleterious) effects lead to a later discharge from the w.c. and hence to deterioration of the transport performance in the drainage system." Ibid Moreover, toilet testing procedure standards reflect this mechanism of action as set forth in another publication: "(d) Drop four test pieces into the water area of the bowl of the pan from a point level with the top of the rim using directing device according to FIG. C8. (e) Activate the full-flush mechanism of the cistern or flush valve to flush the pan and observe discharge to establish when the last of four test pieces have discharged from the outlet spigot of the pan. The trailing volume water is then determined using s suitable measuring device (see FIG. C7)." (Australian Standard Water closets of 6/3 L capacity; AS1172.2-1993 Appendix C, C5 (d), (e)) And further: "(c) Use the paper crumpling device in the sequence shown in FIGS. A2 to A8 for six pieces of paper. All six pieces of paper shall be dropped into the bowl at the same time. (d) With the cistern filled to the nominated working level and the water supply (if connected), turned off, activate the flush valve or cistern to discharge the pan 10 +0, −5 s after the paper is dropped into the bowl. Record the number of pieces of paper fully discharged from the outlet." Ibid Standards for testing the designed flushability of sanitary products also reflect this mechanism, as set forth a publication: "G. (a) The product should be held vertically and the bottom of the pad (not loops) should be level with the rim of the toilet and in the centre of the basin. H. (b) The product is dropped into the pan and 20 seconds later the toilet is flushed." Supra, Howarth et. al at page 4.

In contradistinction to prior art, the invention is specifically designed to utilize a heretofore unrecognized method of flushing where the operative force for the movement of the diaper out of the toilet and through the drain trap is traction or pulling of the diaper from its distal or leading end. In this invention, when the elongated body is flushed, only a small portion is passing through the drain trap at any one time, minimizing the risk of blockage. The relative wetted area of the leading end of the diaper compared to the trailing remainder of the diaper (at least a two to one (2:1) length to width ratio) causes sufficient drag or friction in the rapidly advancing charge of flushed water to keep the diaper oriented in a linear manner, remaining elongated as it travels through the drain trap and along the drain pipe. To assist in this process the diaper is made of a material that does not absorb, wick, swell and clump as does, for example, ordinary toilet paper. The fibres of the nonwoven material, although permeable to moisture, do not individually swell appreciably with the absorption of moisture, nor appreciably lose their stiffness when wetted. They are also of a material with a specific gravity of less than one, allowing them to float in the advancing charge of flushed water. Being lighter than water, the elongated diaper does not settle and cause obstruction where the water flow is less pronounced in the myriad twists and turns of the waste pipe.

Also, in contradistinction to prior art, traction is applied to the elongated diaper as the toilet is flushed, and then oriented precisely into the current of the departing charge of water, the wetted surface area of the distal end pulling the elongated diaper through the drain trap and drainpipe. The elongated diaper is designed to be long enough (at least twice the original diaper length) for the distal end to reach clear through the drain trap whilst the proximal end is still manually retained in traction above the flushing water. When the proximal end is released, this distal wetted area then continues to pull the elongated diaper completely clear of the drain trap, preventing blockage.

As it continues floating the PVOH film 31 quickly dissolves in the wastewater because significant portions of the insoluble coating have been removed allowing the water to penetrate and dissect between the remaining insoluble surface coating layers. Since the PVOH film 31 provides sole supportive structural integrity to the durable water insoluble continuous coating 4 and additional layer of adhesive 8 (if present), they fracture into small (less than 5 mm across) flakes of inert material. The interspersed flocking covering 6 breaks into clumps of, and individual, fibres. If, for some reason, the diaper were to block the toilet or drain, even momentarily, the diaper continues to dissolve in the flowing water, clearing the block.

Additionally, in FIG. 3 when tear strip 11 is peeled away from the diaper, it simultaneously tears through the segmented receiving frontal tape 24, physically separating it into smaller, more easily flushed pieces. Said frontal tape 24 is segmented into multiple small pieces, in contrast to a single large unit frontal tape known in the art. The adhesive used in the manufacture of the segmented frontal tape 24 and fastening tabs 25 is water soluble, polyvinyl acetate glue or similar water based adhesive. Said segmentation of the receiving frontal tape, and the water soluble glue used in its manufacture as well as that of the fastening tabs enables these parts of the diaper to dissolve into small pieces in the wastewater.

What is claimed is:

1. A unitary, completely toilet flushable, wastewater dissolving absorbent article comprising: a liquid impervious back sheet having one surface, a liquid pervious top sheet having an other surface forming a closed envelope with the back sheet; an absorbent body interposed between the back sheet and top sheet within the envelope; a durable water insoluble continuous coating on both surfaces; the liquid impervious back sheet being made of a water soluble film providing sole supportive structural integrity to the coating on both surfaces; the article having an original length to width ratio, a weakened tear path structure in the article for enabling change in the original length to width ratio by tearing along the weakened tear paths into multiple contiguous parts, the article being capable of elongating preparatory to flushing, means for applying traction to the elongated article for controlling the article's orientation as it is flushed down a toilet, and means for removing a portion of the coating to allow dissolution of the back sheet comprising an adhesive material which when manually removed from the liquid impervious back sheet peels the durable water insoluble continuous coating from the underlying soluble film.

2. A unitary, completely toilet flushable, wastewater dissolving absorbent article comprising: a liquid impervious back sheet having one surface, a liquid pervious top sheet having an other surface forming a closed envelope with the back sheet; an absorbent body interposed between the back sheet and top sheet within the envelope; a durable water insoluble continuous coating on both surfaces; the liquid impervious back sheet being made of a water soluble film providing sole supportive structural integrity to the coating on both surfaces; the article having an original length to width ratio, a weakened tear path structure in the the article for enabling change in the original length to width ratio by tearing along the weakened tear paths into multiple contiguous parts, the article being capable of elongating preparatory to flushing, means for applying traction to the elongated article for controlling the article's orientation as it is flushed down a toilet, and interspersed flocking like material adhered to the durable water insoluble continuous coating of said liquid impervious back sheet.

* * * * *